(12) United States Patent
Ohtomo et al.

(10) Patent No.: US 6,979,461 B1
(45) Date of Patent: Dec. 27, 2005

(54) METHOD FOR PRODUCING LIPOSOME PREPARATION

(75) Inventors: Kazumi Ohtomo, Ibaraki (JP); Hajime Konno, Takatsuki (JP); Akihiro Kasai, Ikoma (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 229 days.

(21) Appl. No.: 10/089,084

(22) PCT Filed: Oct. 3, 2000

(86) PCT No.: PCT/JP00/06852

§ 371 (c)(1),
(2), (4) Date: Apr. 10, 2002

(87) PCT Pub. No.: WO01/28522

PCT Pub. Date: Apr. 26, 2001

(30) Foreign Application Priority Data

Oct. 18, 1999  (JP) .................................. 11-295834

(51) Int. Cl.$^7$ ............................................. A61K 9/127
(52) U.S. Cl. ...................... 424/450; 264/4.1; 264/4.3; 264/4.6
(58) Field of Search ................................ 424/450, 1.21, 424/9.321, 9.51, 417; 264/4.1, 4.3, 4.6

(56) References Cited

U.S. PATENT DOCUMENTS 4,532,130 A  7/1985  Djordjevich et al.

FOREIGN PATENT DOCUMENTS

| EP | 0 357 005 | 3/1990 |
|----|-----------|--------|
| EP | 0 658 344 | 6/1995 |
| JP | 06 315623 | 11/1994 |
| WO | 86 01103  | 2/1986 |
| WO | 92 22298  | 12/1992 |

Primary Examiner—Gollamudi S. Kishore
(74) Attorney, Agent, or Firm—Leydig, Voit & Mayer, Ltd.

(57) ABSTRACT

An object of the present invention is to provide a method for producing a liposome preparation having excellent rapid action and excellent redispersion into aqueous medium. The present invention provides a method for producing a liposome preparation by vacuum drying wherein liposome condensed solution, which is obtained by removing solvent from liposome solution, is subjected to vacuum drying without freezing while bubbling the condensed solution or after the condensed solution is bubbled.

8 Claims, No Drawings

METHOD FOR PRODUCING LIPOSOME PREPARATION

TECHNICAL FIELD

This invention relates to a pharmaceutical liposome preparation comprising, as an active ingredient, a pipecolic acid derivative whose excellent immunosuppressive activity has attracted special interest lately, particularly a macrolide compound, for example, tricyclic compound known as tacrolimus (FK506) or a pharmaceutically acceptable salt thereof. More particularly, the present invention relates to a liposome preparation comprising the above active ingredient stably entrapped into liposomes and as a consequence capable of maintaining stable solution in various media such as physiological saline, glucose solution for injection, water or juices and, hence, being applicable to various methods of administration including injections such as intravenous injection, intramuscular injection, and topical injections for intraarticular and the like, topical administration such as application to skin, instillation into eye, nasal administration, and inhalation, and further, oral administration and rectal administration etc. In particular, a liposome preparation of the present invention is characterized in that the dried liposome preparation of the invention has excellent clarity and forms no precipitate even when redispersed into aqueous medium such as blood plasma. Also the present invention relate to a method for producing the same.

BACKGROUND ART

As a liposome preparation containing tacrolimus, for example, there have been known those prepared by incorporating a stabilizer such as cholesterol into phospholipid as a principal ingredient for forming liposome (WO93/08802). With such a constitution, it becomes possible to prepare a liquid preparation from tacrolimus, which is slightly soluble in water. Even if such a preparation is contacted with a body fluid, crystallization of an active ingredient does not yield so that the preparation exhibits excellent bioavailability and is stable. Therefore, the preparation can take any dosage form represented by injection, instillation into eye, nasal administration, inhalation, percutaneous absorbent, topical injection and the like. Furthermore, it also becomes possible to enhance intensive transmigration of tacrolimus to a site where transmigration of tacrolimus is particularly desired, and to suppress its transmigration to a site where transmigration is not necessarily desired. It is known that excellent effects in practice, such as enhancement of drug efficacy, reduction of side effects and persistence of drug efficacy are obtained as a result.

The liposome preparation exhibits an excellent effect to treatment of cerebral ischemic diseases such as cerebral infarction. However, since a liposome membrane is too stable, the liposome preparation tend to exhibit insufficient rapid action, like an anticoagulant, a fibrinolytic agent and a cerebrovascular dilator used as a medical treatment to cerebral infarction. Therefore, it has been required to develop a drug having an excellent rapid action capable of coping with an emergent situation such as cerebral infarction and also having an excellent redispersion property.

An object of the present invention is to improve the problems described above, thereby to provide a liposome preparation having excellent rapid action and excellent redispersion into an aqueous medium.

DISCLOSURE OF THE INVENTION

The present invention provides a method for producing the liposome preparation by vacuum drying characterized in that liposome condensed solution obtained by removing solvent from a liposome solution is subjected to vacuum drying without freezing while bubbling the condensed solution or after bubbling the condensed solution. And also the present invention provides a liposome preparation produced by the method of this invention. An active ingredient for use in the present invention is not specifically limited as long as the active ingredient is applicable to the liposome preparation. As an active ingredient, preferably a pipecolic acid derivative, more preferably a macrolide compound exemplified by a tricyclic compound of the following general formula (I) or a pharmaceutically acceptable salt thereof entrapped into liposomes is used. With a preferred constitution, lecithin is mainly used as a liposome-forming lipid and the preparation containing no cholesterol as a stabilizer is preferable.

A liposome preparation containing, as an active ingredient, 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone of the following formula (I) or a pharmaceutically acceptable salt thereof; and as a liposome-forming lipid, lecithin is particularly preferred.

In the present invention, special attention is paid to the fact that the pipecolic acid derivative, particularly macrolide compound used in the liposome preparation has nerve protection action, and it is expected that the macrolide compound exhibits drug efficiency of protecting further necrosis of nerves and cells on the periphery of cerebral cells whose necrosis was caused by cerebral thrombosis. However, the use as a drug is not limited thereto as a matter of course.

The pipecolic acid derivative in the present invention means those, which has a common activity capable of having an affinity for FKBP type-immunophilin and inhibiting peptidyl-proryl isomerase and/or rotamase enzyme activity, and which have an common chemical structure capable of being a derivative of pipecolic acid.

Specific example of the pipecolic acid derivative include a macrolide compound such as tricyclic compound of the following general formula (I) or a pharmaceutically acceptable salt thereof:

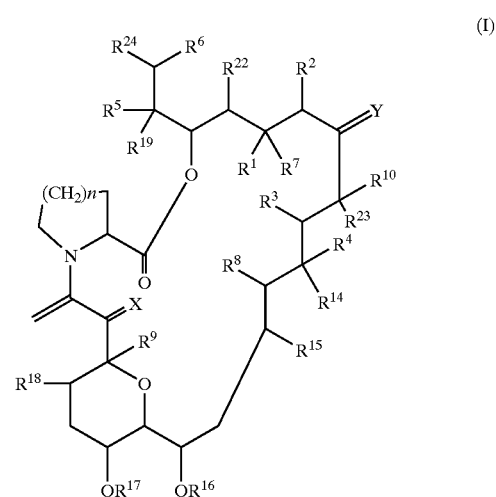

(I)

wherein each of adjacent pairs of $R^1$ and $R^2$, $R^3$ and $R^4$, and $R^5$ and $R^6$ independently:

(a) is two adjacent hydrogen atoms; or
(b) may form another bond formed between the carbon atoms to which they are attached; and $R^2$ may also be an alkyl group;

$R^7$ is a hydrogen atom, a hydroxy group, a protected hydroxy group, an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, a state where a hydrogen atom and a hydroxy group are attached to one carbon atom, a state where two hydrogen atoms are attached to one carbon atom, or a group represented by the formula —CH$_2$O—;

Y is an oxo group, a state where a hydrogen atom and a hydroxy group are attached to one carbon atom, a state where two hydrogen atoms are attached to one carbon atom, or a group represented by the formula =N—NR$^{11}$R$^{12}$ or N—OR$^{13}$;

$R^{11}$ and $R^{12}$ are independently a hydrogen atom, an alkyl group, an aryl group, or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring which may contain one or more hetero atoms; and n represents an integer of 1 or 2.

In addition to the above definitions, Y, $R^{10}$ and $R^{23}$ together with the carbon atoms to which they are attached, may be a saturated or unsaturated 5- or 6-membered heterocycic ring containing nitrogen, sulfur and/or oxygen atoms, and the heterocyclic ring may be substituted with one or more groups selected from the group consisting of an alkyl, a hydroxy, an alkyloxy, a benzyl, a group of the formula —CH$_2$Se(C$_6$H$_5$), and an alkyl substituted by one or more hydroxy groups.

The definitions used in the above general formula (I), and specific examples and preferred examples thereof are explained and set forth in detail.

The term "lower" means, unless otherwise indicated, a group having 1 to 6 carbon atoms.

Preferable examples of the "alkyl group and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl group include a straight or branched chain aliphatic hydrocarbon residue having one double-bond, for example, a lower alkenyl group such as vinyl, propenyl (e.g., allyl), butenyl, methylpropenyl, pentenyl and hexenyl.

Preferable examples of the "aryl group" include phenyl, tolyl, xylyl, cumenyl, mesityl and naphthyl.

Preferable protective groups in the "protected hydroxy groups" and in a "protected amino" described later include 1-(lower alkylthio)(lower)alkyl group such as a lower alkylthiomethyl group (e.g. methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

tri-substituted silyl group such as a tri(lower)alkylsilyl (e.g., trimethylsilyl, triethylsilyl, tributylsilyl, tert-butyldimethylsilyl, tri-tert-butylsilyl, etc.) or a lower alkyl-diarylsilyl (e.g., methyldiphenylsilyl, ethyldiphenylsilyl, propyldiphenylsilyl, tert-butyldiphenyl-silyl, etc.), more preferably tri($C_1$–$C_4$)alkylsilyl group and $C_1$–$C_4$ alkyldiphenylsilyl group, most preferably tert-butyldimethylsilyl group and tert-butyldiphenylsilyl group; and an acyl group such as aliphatic, aromatic acyl group or aliphatic acyl group substituted by an aromatic group, which are derived from carboxylic acid, sulfonic acid or carbamic acid.

Examples of the aliphatic acyl group include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.;

a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl(lower)alkoxycarbonyl (lower)alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and the like.

Examples of the aromatic acyl group include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$c_4$)alkanoyl group having two ($C_1$–$C_4$) alkyls at the cycloalkyl moiety, camphorsulfonyl group, carboxy-($C_1$–$C_4$)alkylcarbamoyl group, tri($C_1$–$C_4$) alkylsilyl($C_1$–$C_4$)alkoxycarbonyl($C_1$–$C_4$)-alkylcarbamoyl group, benzoyl group optionally having one or two nitro groups, benzenesulfonyl group having halogen, or phenyl ($C_1$–$C_4$)alkanoyl group having $C_1$–$C_4$alkoxy and trihalo ($C_1$–$C_4$)alkyl group. Among these, most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl 2-methoxy-2-phenylacetyl.

Preferable examples of the "saturated or unsaturated, 5- or 6-membered heterocyclic ring containing nitrogen, sulfur and/or oxygen atoms" include a pyrrolyl group and a tetrahydrofuryl group.

$R^{24}$ is an optionally substituted ring which may contain one or more hetero atoms, and preferable $R^{24}$ may be cyclo($C_{5-7}$)alkyl group, which may be substituted with suitable substituents and the following ones can be exemplified:
(a) a 3,4-di-oxo-cyclohexyl group,
(b) a 3-$R^{20}$–4-$R^{21}$-cyclohexyl group, in which $R^{20}$ is hydroxy, an alkoxy group, an oxo group, or a —$OCH_2OCH_2CH_2OCH_3$ group, and $R^{21}$ is hydroxy, —OCN, an alkoxy group, a heteroaryloxy which may be substituted by suitable substituents, 1-tetrazolyl, 2-tetrazolyl, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}CHCOO$— (in which $R^{25}$ is optionally protected hydroxy or protected amino, and $R^{26}$ is hydrogen or methyl, or $R^{20}$ and $R^{21}$ combine each other to form an oxygen atom in an epoxide ring; or
(c) a cyclopentyl group, substituted by methoxymethyl, optionally protected hydroxymethyl, acyloxymethyl (in which the acyl moiety optionally contains either an optionally contains either dimethylamino group, which may be quaternized, or carboxy group which may be esterified one or more amino and/or hydroxy groups which may be protected, or aminooxalyloxymethyl.

A preferred example is a 2-formyl-cyclopentyl group.

A "heteroaryl which may be substituted by suitable substituents" moiety of the "heteroaryloxy which may be substituted by suitable substituents" may be the ones exemplified for $R^1$ of the compound of the formula I of EP-A-532, 088, with preference given to 1-hydroxyethylindol-5-yl, the disclosure of which is incorporated herein by reference.

The tricyclic compound (I) and its pharmaceutically acceptable salt for use in the present invention are well known to have excellent immunosuppressive activity, antimicrobial activity and other pharmacological activities and, as such, be of value for the treatment or prevention of rejection reactions by transplantation of organs or tissues, graft-vs-host reaction, autoimmune diseases, and infectious diseases with a method of production of them [EP-A-0184162, EP-A-0323042, EP-A-423714, EP-A-427680, EP-A-465426, EP-A-480623, EP-A-532088, EP-A-532089, EP-A569337, EP-A-626385, WO89/05303, WO93/05058, WO96/31514, WO91/13889, WO91/19495, WO93/04680, WO93/5059, etc.], the disclosures of which are incorporated herein by reference.

Particularly, the compounds which are designated as tacrolimus, FR900520 (ascomycin), FR900523, and FR900525 are products produced by microorganisms of the genus *Streptomyces*, such as *Streptomyces tsukubaensis* No. 9993 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Oct. 5, 1984, accession number FERM BP-927] or *Streptomyces hygroscopicus* subsp. *yakushimaensis* No. 7238 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Jan. 12, 1985, accession number FERM BP-928][EP-A-0184162]. The tacrolimus of the following chemical formula, in particular, is a representative compound.

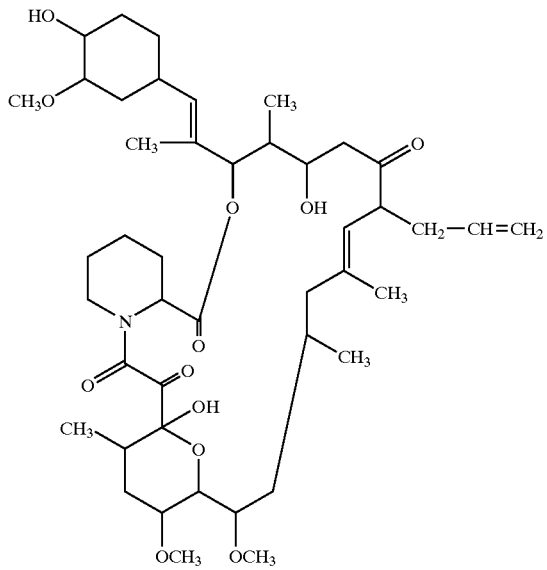

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone.

Preferred examples of the tricyclic compounds (I) are ones wherein each of adjacent pairs of $R^3$ and $R^4$, and/or $R^5$ and $R^6$ independently form another bond formed between the carbon atoms to which they are attached;

Each of $R^8$ and $R^{23}$ is independently a hydrogen atom;

$R^9$ is a hydroxy group;

$R^{10}$ is a methyl group, an ethyl group, a propyl group or an allyl group;

X is an oxo group, a state where a hydrogen atom and a hydroxy group are attached to one carbon atom, a state where two hydrogen atoms are attached to one carbon atom, or an oxo group;

Y is an oxo group;

Each of $R^{14}$, $R^{15}$, $R^{16}$, $R^{17}$, $R^{18}$, $R^{19}$ and $R^{22}$ is a methyl group;

$R^{24}$ is a 3-$R^{20}$–4-$R^{21}$-cyclohexyl group, in which $R^{20}$ is hydroxy, an alkoxy group, an oxo group, or a —$OCH_2OCH_2CH_2OCH_3$ group, and $R^{21}$ is hydroxy, —OCN, an alkoxy group, a heteroaryloxy which may be substituted by suitable substituents, 1-tetrazolyl, 2-tetrazolyl, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}CHCOO$—, in which $R^{25}$ is optionally protected hydroxy or protected amino, and R is hydrogen or methyl, or $R^{20}$ and $R^{21}$ together form an oxygen atom in an epoxide ring; and n is an integer of 1 or 2.

Most preferable tricyclic compounds (I) are, in addition to tacrolimus, ascomycin derivatives such as halogenated-ascomycin (ASM 981) (e.g., 33-epi-chloro-33-desoxyascomycin), which is disclosed in EP-A-427,680, example 66a, 32-O-(1-hydroxyethylindol-5-yl)ascomycin (L-732,531), which is disclosed in EP-A-532,088, 32-(1H-tetrazolyl-1-yl)ascomycin (ABT281), which is disclosed in WO93/04680, etc.

As the other preferable examples of the macrolide compound, rapamycin [THE MERCK INDEX (12th edition), No. 8288] and its derivatives can be examplified. Preferred example of the derivatives is an O-substituted derivative in which the hydroxy in the position 40 of formula A illustrated at page 1 of WO 95/16691 is replaced by —OR$_1$ in which R$_1$ is hydroxyalkyl, hydroalkoxyalkyl, acylaminoalkyl or aminoalkyl, for example, 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin.

These O-substituted derivatives may be produced by reacting rapamycin (or dihydro or deoxo-rapamycin) with an organic radical attached to leaving group (for example, RX where R is an organic radical which is desired as the O-substituent, such as an alkyl, allyl, or benzyl moiety, and X is leaving group such as CCl$_3$C(NH)O or CF$_3$SO$_3$) under suitable reaction conditions.

The conditions may be acidic or neutral conditions, for example in the presence of an acid like trifluoromethanesulfonic acid, camphorsulfonic acid or p-toluenesulfonic acid or their respective pyridinium or substituted pyridinium salts when X is CCl$_3$C(NH)O, or in the presence of a base like pyridine, substituted pyridine, diisopropylethylamine or pentamethylpiperidine when X is CF$_3$SO$_3$.

Most preferable rapamycin derivative is 40-O-(2-hydroxy)ethyl rapamycin, which is disclosed in WO94/09010, the disclosure of which is incorporated herein by reference.

The tricyclic compound (I), and rapamycin and its derivatives have a similar basic structure, i.e. tricyclic macrolide structure, and at least one of similar biological properties (or example, immunosupressive activity).

The pharmaceutically acceptable salt of the tricyclic compound (I) and rapamycin and its derivatives may be a conventional non-toxic and pharmaceutically acceptable salt, such as salt with inorganic or organic bases, specifically an alkali metal salt such as sodium salt and potassium salt, alkali earth metal salt such as calcium salt and magnesium salt, ammonium salt, and amine salt such as triethylamine salt and N-benzyl-N-methylamine salt.

With respect to the pipecolic acid derivatives and macrolide compounds used in the present invention, it is to be understood that there may be conformers, and one or more pairs of stereoisomers such as optical isomers due to asymmetric carbon atom(s) and geometrical isomers due to double bonds, and such conformers and isomers are also included within the scope of the present invention. Furthermore, the pipecolic acid derivatives and macrolide compounds can in the form a solvate, which is also included within the scope of the present invention. The solvate preferably includes, for example, a hydrate and an ethanolate.

In addition, examples of the pipecolic acid derivatives, which can be used for the object of the present invention, include the followings:

(1) the following Way-124466 compounds synthesized by the reaction between 4-fenyl-1,2,4-triazolin-3,5-dion and rapamycin (Ocain et al., Biochemical and Biophysical Research Communications. Vol. 192, No.3, 1993);

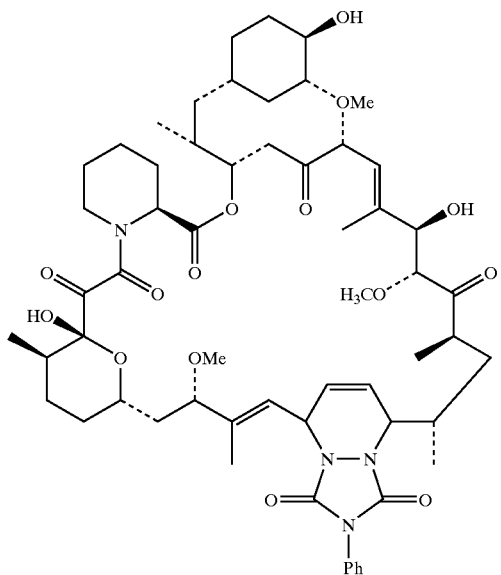

(2) pipecolic acid derivative compounds referred to as RAP-Pa (Charkraborty et al., Chemistry and Biology, March 1995, 2: 157–161);

(3) the following pipecolic acid derivative compounds (Ikeda et al., J. Am. Chem. Soc. 1994, 116, 4143–4144);

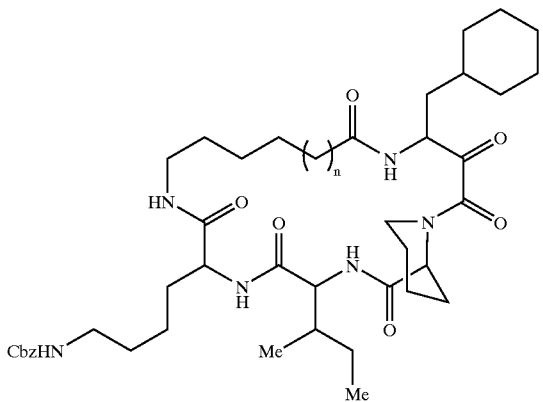

n = 1, 2, or 3

(4) Wang et al., Bioorganic and Medicinal Chemistry Letters, Vol. 4, No. 9, pp. 1161–1166, 1994, particularly pipecolic acid derivative compounds disclosed as the compounds 2a–2d;

(5) the following pipecolic acid derivative (Birkenshaw et al., Bioorganic and Medicinal Chemistry Letters, Vol. 4, No.21, pp. 2501–2506, 1994);

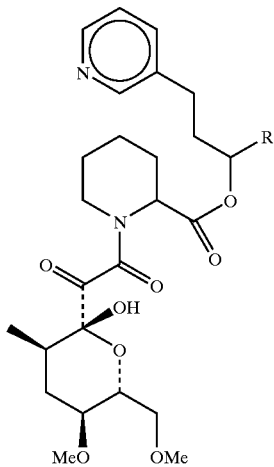

(6) Holt et al., J. Am. Chem. Soc. 1993, 115, 9925–9938, particularly pipecolic acid derivative compounds disclosed as the compounds 4–14;
(7) pipecolic acid derivative compounds disclosed in Caffer et al., Bioorganic and Medicinal Chemistry Letters, Vol. 4, No.21, pp. 2507–2510, 1994;
(8) pipecolic acid derivative compounds disclosed in Teague et al., Bioorganic and Medicinal Chemistry Letters, Vol. 3, No.10, pp. 1947–1950, 1993;
(9) Yamashita et al., Bioorganic and Medicinal Chemistry Letters, Vol. 4, No.2, pp. 325–328, 1994, particularly pipecolic acid derivative compounds disclosed as the compounds 11, 12 and 19;
(10) Holt et al., Bioorganic and Medicinal Chemistry Letters, Vol. 4, No.2, pp. 315–320, 1994, in particular pipecolic acid derivative compounds disclosed as the compounds 3–21 and 23–24;
(11) Holt et al., Bioorganic and Medicinal Chemistry Letters, Vol. 3, No.10, pp. 1977–1980, 1993, particularly pipecolic acid derivative compounds disclosed as compounds 3–15;
(12) Hauske et al., J. Med. Chem. 1992, 35, 4284–4296, particularly pipecolic acid derivative compounds disclosed as the compounds 6, 9–10, 21–24, 26, 28, 31–32 and 52–55;
(13) pipecolic acid derivatives disclosed in Teague et al., Bioorganic and Medicinal Chemistry Letters, Vol. 4, No.13, pp. 1581–1584, 1994; and
(14) Stocks et al., Bioorganic and Medicinal Chemistry Letters, Vol. 4, No.12, 1457–1460, 1994, particularly pipecolic acid derivative compounds disclosed as the compounds 2, 15–17.

The liposome preparation of the present invention can be produced by vacuum drying a liposome condensed solution, which is obtained by removing solvent from liposome solution, while bubbling the condensed solution or after bubbling the condensed solution.

The liposome condensed solution can be bubbled by changing the condensed solution condition from stability to instability condition under vacuum. As one example, the bubble may be generated by thermal change, and more specifically by raising a temperature of the condensed solution after lowering the temperature of the condensed solution under vacuum condition. Such a thermal change of the condensed solution is not specifically limited but raising the temperature of the condensed solution to 20° C. or more after lowering the temperature of the condensed solution to minus 10° C. or lower is recommended, and raising the temperature of the solution to the range from 20° C. to 70° C. after lowering the temperature of the solution to minus 10° C. or lower is preferable. More preferably, raising the temperature of the solution to the range from 25° C. to 60° C. after lowering the temperature of the solution to the range from minus 20° C. to minus 50° C. is recommended, and the most preferably, raising the temperature of the solution from 30° C. to 50° C. after lowering the temperature of the solution to minus 30° C. to minus 40° C.

As another example, the bubble may be generated by setting the condensed solution under vacuum condition while flowing the condensed solution or after flowing the condensed solution. For example, the condensed solution may be flowed by inclining a container filled with the condensed solution.

When the bubble is generated by the thermal change or by the flowing, the bubble is preferably generated while keeping the condensed solution in its liquid phase.

The vacuum drying method of the invention is preferably conducted by applying conventional operating condition while keeping the condensed solution in its liquid phase. The "vacuum" herein means at least medium vacuum condition and does not necessarily means complete vacuum condition.

According to the present invention, the freeze drying method, which may be resulted in lowering clarity when freeze dried liposome preparation is re-dispersed into aqueous medium such as blood plasma, should be avoided and vacuum drying method without freezing the condensed solution is recommended.

As an essential condition, the liposome preparation of the present invention is obtained by the above mentioned production process, and other conditions such as structure, composition, constituent ingredients, preparation process, size of liposomes, and the types of compounds that may be used in combination with liposomes are not specifically limited unless these conditions adversely affect a rapid action of drug and unless these conditions ensure stable entrapping of the pipecolic acid derivatives into liposomes. Thus, the structure of liposome may be a large unilamellar vesicle (LUV), a multilamellar vesicle (MLV) or a small unilamellar vesicle (SUV). Therefore, the size may be within the range from 200 to 1000 nm for LUV, from 400 to 3500 nm for MLV, and from 20 to 50 nm for SUV in particle diameter. SUV which exhibits low accumulation into a reticroendothelial system (RES) is preferred.

As the liposome constituting the liposome structure, phospholipids and nitrolipids are used. In general, phospholipids are preferred. Examples thereof include natural phospholipids such as egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanolamine, phosphatidyl glycerol, diphosphatidyl glycerol, cardiolipin, plasmalogen, and so on or hydrogenation products obtainable from said phospholipids by the conventional technology; and synthetic phospholipids such as dicetyl phosphate, distearoylphosphatidyl choline, dipalmitoylphosphatidyl choline, dipalmitoylphosphatidyl ethanolamine, dipalmitoylphosphatidyl serine, eleostearoylphosphatidyl choline, eleostearoylphosphatidyl ethanolamine, eleostearoylphosphatidyl serine, and so on, more preferred ones are lecithins, and the most preferred one is egg yolk lecithin.

Lipids including these phospholipids can be used alone, or two ore more kinds of them can be used in combination. In this case, lipids in which the electronegative group in the phosphatidly group and the electropositive group in the atomic group (ethanolamine, choline and so on) bound thereto are electrically balanced so that the whole molecule is electrically neutral. For example, lecithins, sphingomyelin, phosphatidyl ethanolamine, distearoylphosphatidyl choline and so on are often used alone. In contrast, lipids which are electronegative as a whole, in which the atopic group (such as serine, glycerol, inositol or the like) combined to the phosphatidyl group (electronegative group) is electrically neutral, for example, phosphatidylserine, phosphatidylglycerol, phosphatidylinositol, and so on or lipids such as phosphatidic acid or dicetyl phosphate which are electronegative, can be used independently as the lipid in this invention, but it is rather recommended that they are used in combination with the neural lipid such as those mentioned above. Among them, phosphatidic acid and dicetylphosphate do not act as the principal phospholipid in the formation of liposome but are known as liposome forming additives. Considering the stability and handling of liposome preparation in the present invention, additives such as excipients and/or stabilizers can preferably be used.

Stabilizers used preferably in the present invention include, for example, lactose, maltose, stearylamine, α-tocopherol, gangliosoide, acid glycolipid sulfatides, and a kind of acidic glycolipid and glycolipids having a sulfuric acid group.

When liposome preparation is prepared by incorporating a stabilizer such as cholesterol, a rapid action can be hardly obtained in the same level as that to be required in the present invention and cholesterols are generally likely to exert undesired influence on cerebral infraction. Therefore, instead of cholesterols, lactose and maltose are preferably used as a stabilizer in the present invention.

Surface active agents such as polyoxyethylene hardened castor oil surface active agent (HCO-60) can be used as a recrystallization inhibitor of the macroride compound but the surface active agents may be exert undesired influence on affected areas like brain. Therefore, recrystallization inhibitor is preferably not used in the present invention.

BEST MODE FOR CARRYING OUT THE INVENTION

Examples

The examples of the present invention will be illustrated but the present invention is not limited to the following examples, and modifications can be made without departing from the purports described hereinabove and hereinafter and are also included in the technical scope of the present invention.

Example 1

Tacrolimus (5 g) and α-tocopherol (0.3 g) were dissolved in adequate amount of ethanol to obtain 100 mL of a mixed solution. After egg yolk lecithin (100 g) was dissolved into the mixed solution, ethanol in the solution was removed at 40° C. under 1330 Pa. Thus obtained solution was roughly dispersed into 10 liter of 10% maltose aqueous solution (about 10.3 kg) by stirrer to obtain roughly dispersed solution.

After the dispersed solution was emulsified by high pressure emulsifying apparatus (DeBee 2000 manufactured by DeBee Co., Israel) under 241325 kPa of emulsification pressure and 13790 kPa of back pressure, the dispersion was sterile filtered through a 0.22 μm filter. About 10.4 g of the filtrate was charged into a vial (the vial was washed and cleaned before charging the filtrate). The vacuum rubber stopper is pressed into the vial (up to half of the stopper) and the vial is put into the freeze dry machine. The machine was operated at 25 under 3990 Pa to deaerate gas dissolved in the filtrate. The deaerated filtrate was condensed at 40° C. under 1330 Pa to obtain condensed solution. The condensed solution was cooled to −40° C. and the solution was bubbled by raising the temperature of the solution to 40° C. under high vacuum condition (1.33 Pa). The bubbled solution was vacuum dried at 30° C. under 13.3 Pa and then the vial was hermetically sealed after the solution was pressurized to atmospheric pressure with nitrogen gas. The properties of thus obtained liposome preparation will be shown in Table 1.

Comparative Example 1

Freeze Drying Method

Tacrolimus (5 g) and α-tocopherol (0.3 g) were dissolved in adequate amount of ethanol to obtain 100 mL of a mixed solution. After egg yolk lecithin (100 g) was dissolved into the mixed solution, ethanol in the solution was removed at 40° C. under 1330 Pa. Thus obtained solution was roughly dispersed into 10 liter of 10% maltose aqueous solution (about 10.3 kg) by stirrer to obtain roughly dispersed solution.

After the dispersed solution was emulsified by high pressure emulsifying apparatus (DeBee 2000) under 241325 kPa of emulsification pressure and 13790 kPa of back pressure, the dispersion was sterile filtered through a 0.22 μm filter. About 10.4 g of the filtrate was charged into a vial (the vial was washed and cleaned before charging the filtrate) and freeze dried. The properties of thus obtained liposome preparation will be shown in Table 1.

TABLE 1

| | Comparative Example 1 | Example 1 |
| --- | --- | --- |
| Drying Method | Freeze dry | Vacuum dry |
| Appearance (color) | lump (white) | Bubbly lump (white) |
| Content*1 | 4.99 | 4.91 |
| Water amount (%)*2 | 0.4 | 4.1 |
| Time needed for redispersion (sec)*3 | 15 | 15 |
| pH*4 | 5.45 | 5.82 |
| Permeability*5 | 4.9 | 66.8 |
| Average particle diameter (nm)*6 | 91 | 42 |
| Precipitate in the blood plasma*7 | Exist | Non |
| Precipitate in the physiological sodium chloride solution*7 | Exist | Non |
| Filtration pressure (kPa)*8 | 10 or more | 1.3 |

*1Content: amount of tacrolimus (mg/vial) contained in dried liposome preparation was measured by HPLC.
*2Water Amount: amount of water contained in dried liposome preparation was measured by Karl Fischer's method
*3Time needed for redispersion: about 9 mL of water for injection and dried liposome preparation was added to a container and then the container was shaken by hand at an amplitude of 40 cm (2 reciprocation /sec) under room temperature and solubility of the liposome preparation with the water was measure every 15 seconds.
*4pH: pH of the redispersed solution (obtained by dissolving the liposome preparation with water, see *3) was measured by pH electrode.
*5Permeability: permeability of the redispersed solution was measured by spectrophotometer (cell size 1 cm × 1 cm)
*6Average Particle Diameter: average particle diameter of the liposome in the redispersed solution was measured by dynamic light-scattering method.
*7Precipitate: the redispersed solution was mixed with blood plasma or physiological sodium chloride solution at a ratio of 2 to 1 and thus obtained mixed solution was centrifuged and precipitate in the solution was estimated visually.
*8Filtration Pressure: the redispersed solution was filtered through injection type sleeve equipped with 0.22 μm filter and the filtration pressure was measured with autoradiography The liposome preparation produced by the present inventive method contained slightly large amount of water, but the present inventive liposome preparation exhibited excellent permeability after redispersion over the liposome preparation of the comparative example 1 and also the clarity of the present inventive liposome preparation is also better than that of comparative example 1. The liposome preparation of the example 1 formed no precipitate when mixed with blood plasma and kept favorable properties after redispersion.

Example 2

Tacrolimus (5 g) was dissolved in adequate amount of ethanol to obtain 100 mL of a mixed solution. After egg yolk lecithin (100 g) was dissolved into the mixed solution, ethanol in the solution was removed at 40° C. under 1330 Pa. Thus obtained solution was roughly dispersed into 10 liter of 10% maltose aqueous solution (about 10.3 kg) by stirrer to obtain roughly dispersed solution.

After the dispersed solution was emulsified by high pressure emulsifying apparatus (DeBee 2000) under 241325 kPa of emulsification pressure and 13790 kPa of back pressure, the dispersion was sterile filtered through a 0.22 μm filter. About 10.4 g of the filtrate was charged into a vial (the vial was washed and cleaned before charging the filtrate). The vacuum rubber stopper is pressed into the vial (up to half of the stopper) and the vial is put into the freeze dry machine. The machine was operated at 25° C. under 3990 Pa to deaerate gas dissolved in the filtrate. The deaerated filtrate was condensed at 40° C. under 1330 Pa to obtain condensed solution. The condensed solution was cooled to −40° C. and the solution was bubbled by raising temperature of the solution to 40° C. under high vacuum condition (1.33 Pa). The bubbled solution was vacuum dried at 30° C. under 13.3 Pa and then the vial was hermetically sealed after the solution was pressurized to atmospheric pressure with nitrogen gas. Thus obtained liposome preparation exhibited same properties as the liposome preparation of the example 1.

Example 3

In the same manner as in example 2, liposome preparation was obtained from the following prescriptions.

| Tacrolimus | 3 mg |
| Purified egg yolk lecithin | 100 mg |
| Lactose monohydrate | 1000 mg |
| To make | 1103 mg |

Thus obtained liposome preparation of the example 3 exhibited same properties as the liposome preparation of the example 1.

Example 4

In the same manner as in example 1, liposome preparation was obtained from the following prescriptions.

| Tacrolimus | 3 mg |
| Purified egg yolk lecithin | 100 mg |
| α-tocopherol | 0.3 mg |
| Maltose | 1000 mg |
| To make | 1103.3 mg |

Thus obtained liposome preparation of the example 4 exhibited same properties as the liposome preparation of the example 1.

The production method of the present invention can provide the liposome preparation having excellent redispersion into aqueous medium (for example: excellent in clarity after redispersion, narrow distribution range in average particle diameter and forms no precipitate when mixed with blood plasma).

According to the present invention, since liposome can be easily disintegrated as compared with a conventional liposome preparation containing cholesterol, it becomes possible to expect a more excellent rapid action by bolus administration. Furthermore, the preparation of the present invention does not contain a surfactant so that it becomes possible to obtain an excellent effect without exerting any influence on circulatory organs.

INDUSTRIAL APPLICABILITY

Accordingly, the liposome preparation of the present invention is particularly useful for treatment and prevention of diseases wherein a rapid action of drug efficacy is expected, for example, cerebral ischemic diseases (e.g., head injury, hemorrhage in brain (e.g., subarachnoid hemorrhage, intracerebral hemorrhage), cerebral infarction, cerebral thrombosis, cerebral embolism, cardiac arrest, stroke, transient ischemic attack (TIA), hypertensive encephalopathy).

On the basis of the pharmacological effect of a pipecolic acid derivative as an active ingredient, particularly a macrolide compound, for example, tricyclic compound (I), the liposome preparation of the present invention is useful for treatment and prevention of the following diseases and conditions:

rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

infections caused by pathogenic microorganisms (e.g. *Aspergillus fumigatus, Fusarium oxysporum, Trichophyton asteroides*, etc.);

inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves'ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilic gastroenteritis, mastocytosis, Crohn's disease and ulcerative colitis);

food-related allergic diseases with symptomatic manifestation remote from the gastrointestinal tract (e.g. migraine, rhinitis and eczema);

renal diseases (e.g. intestitial nephritis, Goodpasture's syndrome, hemolytic uremic syndrome, diabetic nephropathy), and nephrotic syndrome (e.g. glomerulonephritis);

nervous diseases (e.g. multiple myositis, Guillain-Barre syndrome, Meniere's disease, multiple neuritis, solitary neuritis, cerebral infarctions Alzheimer's disease, Parkinson's disease, amyotrophic lateral sclerosis (ALS) and radiculopathy);

endocrine diseases (e.g. hyperthyroidism, and Basedow's disease);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g. osteoporosis);

respiratory diseases (e.g. sarcoidosis, pulmonary fibrosis, and idiopathic interstitial pneumonia);

skin diseases (e.g. dermatomyositis, leukoderma vulgaris, ichthyosis vulgaris, photosensitivity, and cutaneous T-cell lymphoma);

circulatory diseases (e.g. arteriosclerosis, atherosclerosis, aortitis syndrome, polyarteritis nodosa, and myocardosis);

collagen diseases (e.g. scleroderma, Wegener's granuloma, and Sjogren's syndrome);

adiposis;

eosinophilic fasciitis;

periodontal diseases (e.g. damage to gingiva, periodontium, alveolar bone or substantia ossea dentis);

male pattern alopecia, alopecia senile;

muscular dystrophy;

pyoderma and Sezary syndrome; chromosome abnormality-associated diseases (e.g. Down's syndrome);

Addison's disease;

active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.));

intestinal diseases (e.g. endotoxin shock, pseudomembranous colitis, and drug- or radiation-induced colitis);

renal diseases (e.g. ischemic acute renal insufficiency, chronic renal failure);

pulmonary diseases (e.g. toxicosis caused by pulmonary oxygen or drugs (e.g. paracort, bleomycin, etc.), lung cancer, and pulmonary emphysema); ocular diseases (e.g. cataracta, iron-storage disease (siderosis bulbi), retinitis, pigmentosa, senile plaques, vitreous scarring, corneal alkali burn);

dermatitis (e.g. erythema multiforme, linear immunoglobulin A bullous dermatitis, cement dermatitis);

and other diseases (e.g. gingivitis, periodontitis, sepsis, pancreatitis, and diseases caused by environmental pollution (e.g. air pollution), aging, carcinogen, metastasis of carcinoma, and hypobaropathy)];

diseases caused by histamine release or leukotriene C4 release;

restenosis of coronary artery following angioplasty and prevention of postsurgical adhesions;

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis);

Human Immunodeficiency Virus (HIV) infection, AIDS;

allergic conjunctivitis; and hypertrophic cicatrix and keloid due to trauma, burn, or surgery.

In addition, the macrolide compound such as tricyclic compound (I) has a liver regenerating activity and/or activities of stimulating hypertrophy and hyperplasia of hepatocytes. Therefore, the pharmaceutical composition of the present invention is useful for treatment and prevention of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

Furthermore, the preparation of the present invention is also useful for enhancing the effect of the prevention and/or treatment of various diseases because of the useful pharmacological activity of tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity, and so on.

What is claimed is:

1. A method for producing a liposome preparation comprising tacrolimus or its hydrate by vacuum drying, comprising:

(i) preparing a liposome condensed solution by removing solvent from a liposome solution, which comprises tacrolimus or its hydrate, a liposome-forming lipid, at least one stabilizer and solvent, (ii) subjecting the liposome condensed solution to vacuum drying, wherein under vacuum conditions the temperature of the condensed solution is lowered to the range from −30° C. to −40° C., and then the temperature of the condensed solution is raised to 30° C. to 50° C. to bubble the condensed solution, in which vacuum drying is carried out without freezing while bubbling the condensed solution or after bubbling the condensed solution.

2. The method according to claim 1, wherein the vacuum drying is carried out under 1.33 Pa while bubbling the condensed solution.

3. The method according to claim 1, wherein lecithin is mainly used as the liposome-forming lipid.

4. The method according to claim 3, wherein the liposome contains no cholesterol.

5. The liposome preparation obtained by the method as defined in claim 1.

6. The method of claim 1, wherein the temperature of the condensed solution is raised to 40° C. from −40° C.

7. The method of claim 1, wherein the vacuum drying is carried out under 13.3 Pa after bubbling the condensed solution.

8. The method of claim 1, wherein the stabilizer is one or more selected from lactose, maltose and α-tocopherol.

* * * * *